US011840706B2

(12) United States Patent
Gho

(10) Patent No.: US 11,840,706 B2
(45) Date of Patent: Dec. 12, 2023

(54) COMPOSITION AND METHOD FOR GENERATING A DESIRED CELL TYPE AND/OR TISSUE TYPE FROM HAIR FOLLICULAR STEM CELLS

(71) Applicant: Conradus Ghosal Gho, Bunde (NL)

(72) Inventor: Conradus Ghosal Gho, Bunde (NL)

( * ) Notice: Subject to any disclaimer, the term of this patent is extended or adjusted under 35 U.S.C. 154(b) by 497 days.

(21) Appl. No.: 16/282,444

(22) Filed: Jul. 13, 2023

(65) Prior Publication Data
US 2019/0185811 A1    Jun. 20, 2019

Related U.S. Application Data

(62) Division of application No. 14/764,226, filed as application No. PCT/NL2014/050062 on Feb. 3, 2014, now abandoned.

(30) Foreign Application Priority Data

Feb. 1, 2013  (NL) ...................................... 2010222

(51) Int. Cl.
| A61K 35/12 | (2015.01) |
| C12N 5/071 | (2010.01) |
| C12N 5/0775 | (2010.01) |

(52) U.S. Cl.
CPC ............ *C12N 5/0602* (2013.01); *A61K 35/12* (2013.01); *C12N 5/0628* (2013.01); *C12N 5/0666* (2013.01); *C12N 2500/20* (2013.01); *C12N 2500/24* (2013.01); *C12N 2500/38* (2013.01); *C12N 2500/40* (2013.01); *C12N 2500/44* (2013.01); *C12N 2501/11* (2013.01); *C12N 2501/115* (2013.01); *C12N 2501/13* (2013.01); *C12N 2501/14* (2013.01); *C12N 2501/999* (2013.01); *C12N 2502/11* (2013.01); *C12N 2502/115* (2013.01); *C12N 2506/03* (2013.01); *C12N 2509/00* (2013.01)

(58) Field of Classification Search
CPC .... A61K 35/12; C12N 5/0628; C12N 5/0666; C12N 2500/20; C12N 2501/11; C12N 2501/14; C12N 2502/11; C12N 2502/115
See application file for complete search history.

(56) References Cited

U.S. PATENT DOCUMENTS

| 5,589,376 | A | 12/1996 | Anderson et al. | |
| 6,399,057 | B1* | 6/2002 | Gho | C12N 5/0627 |
| | | | | 424/93.7 |
| 6,974,681 | B1 | 12/2005 | McGrew | |
| 2005/0265980 | A1 | 12/2005 | Chen et al. | |
| 2006/0035290 | A1 | 2/2006 | Popa et al. | |
| 2006/0121016 | A1* | 6/2006 | Lee | A61K 31/7076 |
| | | | | 424/94.1 |
| 2006/0128014 | A1 | 6/2006 | Taggblad et al. | |
| 2007/0122906 | A1* | 5/2007 | Mishra | C12N 5/0656 |
| | | | | 435/372 |
| 2009/0130065 | A1 | 5/2009 | Xu et al. | |
| 2010/0222294 | A1 | 9/2010 | Pelleg | |
| 2010/0279893 | A1 | 11/2010 | Svendsen et al. | |
| 2012/0269781 | A1 | 10/2012 | Ra et al. | |

FOREIGN PATENT DOCUMENTS

| EP | 2275531 A1 | 1/2011 |
| EP | 2502989 A1 | 9/2012 |
| FR | 2876246 A1 | 4/2006 |
| NO | 2012/152717 A1 | 11/2012 |
| WO | 98/47471 A1 | 10/1998 |
| WO | 03/041703 A2 | 5/2003 |
| WO | 2004/018655 A2 | 3/2004 |
| WO | 2005/077285 A1 | 8/2005 |
| WO | 2006/110806 A2 | 10/2006 |
| WO | 2008/004819 A1 | 10/2008 |
| WO | 2009/132156 A1 | 10/2009 |
| WO | 2012/152717 A1 | 11/2012 |
| WO | 2013/007308 A1 | 1/2013 |

OTHER PUBLICATIONS

Sanmartin et al. Selenium Compounds, Apoptosis and Other Types of Cell Death: An Overview for Cancer Therapy. Int. J. Mol. Sci. 2012, 13, 9649-9672 (Year: 2012).*
Kent et al. Bovine Pituitary Extract Provides Remarkable Protection Against Oxidative Stress in Human Prostate Epithelial Cells. In Vitro Cell. Dev. Biol. Animal 39:388-394 (Year: 2003).*
Mahjour et al. Hair Follicle Regeneration in Skin Grafts: Current Concepts and Future Perspectives. Tissue Engineering: Part B vol. 18, No. 1 (Year: 2012).*
Kang et al. Erythropoietin promotes hair shaft growth in cultured human hair follicles and modulates hair growth in mice. Journal of Dermatological Science. vol. 59, Issue 2, Aug. 2010, pp. 86-90 (Year: 2010).*
Gho et al. Human follicular stem cells: their presence in plucked hair and follicular cell culture. British Journal of Dermatology 2004; 150: 860-868 (Year:2004).*
Gho et al. Donor hair follicle preservation by partial follicular unit extraction. A method to optimize hair transplantation. Journal of Dermatological Treatment. 2010; 21:337-349 (Year: 2010).*

(Continued)

*Primary Examiner* — Taeyoon Kim
(74) *Attorney, Agent, or Firm* — Hudak, Shunk & Farine Co. LPA

(57) ABSTRACT

The present invention is concerned with a composition and in vitro method for generating a desired cell type and/or tissue type from hair follicular stem cells. The composition and in vitro method are particularly suitable for generating an autologous desired cell type and/or tissue type. Furthermore, the composition and method are especially efficient and suitable for use in the context of cosmetic cell and/or tissue transplantation in recipient areas of a subject experiencing cell and/or tissue loss caused by, for example, a wound, scar, burn injury, tissue degeneration, and aging. The composition and in vitro method are also suitable to circumvent complications related to infections and/or immune rejection of a cosmetic cell and/or tissue implant or graft.

16 Claims, 1 Drawing Sheet

(56) References Cited

OTHER PUBLICATIONS

Ants Palm-Leis, et al., Mechanisms of Signal Transduction: Mitogen-activated Protein Kinases and Mitogen-activated Protein Kinase Phosphatases Mediate the Inhibitory Effects of All-trans Retinoic Acid on the Hypertrophic Growth of Cardiomyocytes, The Journal of Biological Chemistry, 2004, vol. 279, No. 52, Issue of Dec. 24, pp. 54905-54917, Oct. 18, 2004.
Chun Hua Dai, et al., "Vanadate Mimics the Effect of Stem Cell Factor on Highly Purified Human Erythroid Burst-forming Units in vitro, But Not the Effect of Erythropoieten", Exp. Hematol. 20:1055-1060 (1992).
Gert Rijksen, et al., "The Role of Protein Tyrosine Phosphateses in Density-Dependent Growth Control of Normal Rat Kidney Cells", Federation of European Biochemical Societies, vol. 322, No. 1, 83-87, 1993.
Masahiro Ryuto, et al., "All-trans-retinoic Acid-dependent Inhibition of E-Cadherin-based Cell adhesion with Concomitant Dephosphorylation of β-Catenin in Metastatic Human Renal Carcinoma Cells", Jpn. J. Cancer Res., 88, 982-991, Oct. 1997.
Owen Clark, et al., "Tyrosine Phosphatase Inhibitors Combined with Retinoic Acid Can Enhance Differentiation of Neuroblastoma Cells and Trigger ERK-and AKT-dependent, p53-independent senescence", Cancer Letters, 328, 44-54 2013.
"B27 NeuroMix", PAA the Cell Culture Company, http://www.weike21.com/download/B27-NeuroMix.pdf (retrieved by the European Patent Office on Oct. 7, 2013).
Sigma-Aldrich, "Minimum Essentials Medium Eagle (MEM) Alpha Modifications", Product Information, http://www.sigmaaldrich.com/content/dam/sigma-aldrich/docs/Sigma.Formulation/Mφ984 for. Pdf (retrieved by the European Patent Office on Oct. 7, 2013).
Sigma-Aldrich, "Dulbecco's Modified Eagle's Medium (DME) Alpha Modifications", Product Information, http://www.sigmaaldrich.com/content/dam/sigma-aldrich/docs/Sigma/Formulations/d5546 for. Pdf (retrieved by the European Patent Office on Oct. 7, 2013).
PCT International Search Report for corresponding International Application No. PCT/NL2014/050062, dated May 14, 2014 (7 pages).
PCT International Preliminary Report on Patentability for corresponding International Application No. PCT/NL2014/050062, dated May 14, 2014 (9 pages).
Krenning, G, et al., "CD34+ cells augment endothelial cell differentiation of CD14+ endothelial progenitor cells in vitro", J Cell Mol Med. Aug. 2009; 13(8B):2521-2533. doi: 10.1111/j.1582-4934.2008.00479.x. Epub Aug. 21, 2008. PMID: 18752636; PMCID: PMC6512353.
Pagala, et al., "Extracellular ATP inhibits apoptosis and maintains cell viability by inducing autocine production of interleukin-4 in a myeloid progenitor cell line", International Immunopharmacology 4 (2004) pp. 953-961.
Claudius, Conrad, et al., "Adult Stem Cell Lines in Regenerative Medicine and Reconstructive Surgery", Journal of Surgical Research 124, pp. 201-208 (2005).
Romagnani, Paola, "CD14+CD34low Cell Phenotypic and Functional Features Are the Major Source of Circulating Endothelial Progenitors", Circulation Research Aug. 19, 2005, (97), pp. 314-322.

\* cited by examiner

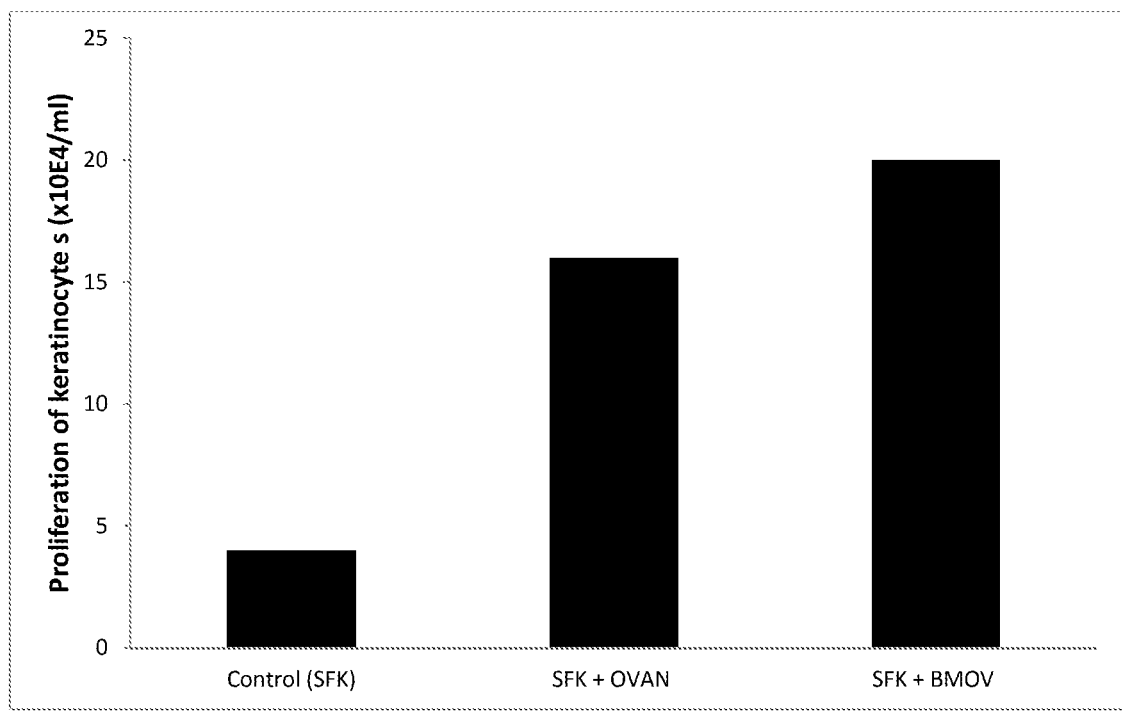

COMPOSITION AND METHOD FOR GENERATING A DESIRED CELL TYPE AND/OR TISSUE TYPE FROM HAIR FOLLICULAR STEM CELLS

CROSS-REFERENCE TO RELATED APPLICATIONS

This application is a divisional of U.S. application Ser. No. 14/764,226, filed Jul. 29, 2015, which is the National Stage of International Application No. PCT/NL2014/050062 filed Feb. 3, 2014, which claims the benefit of Netherlands Application No. NL 2010222, filed Feb. 1, 2013, the contents of which is incorporated by reference herein.

FIELD OF THE INVENTION

The present invention is in the fields of tissue engineering with applications in the fields of cosmetic and aesthetic procedures and regenerative medicine. The present invention provides an improved composition and in vitro method for generating a desired cell type and/or tissue type from at least one hair follicular stem cell. The improved composition and in vitro method of the present invention are particularly suitable for cosmetic or therapeutic cell and/or tissue transplantation in recipient areas of a subject experiencing cell and/or tissue loss caused by a wound, scar, burn injury, tissue degeneration, diseases and/or aging. The composition and in vitro method of the present invention are also particularly suitable to circumvent complications related to infections and/or immune rejection of a cosmetic or therapeutic cell and/or tissue implant or graft in a subject.

BACKGROUND OF THE INVENTION

Interest in pluripotent stem cells has increased dramatically in the last decade, particularly with regards to their role in the rapidly expanding fields of tissue engineering, regenerative medicine, and facial as well as body rejuvenation technology. Natural pluripotent stem cells are cells endowed with the potential to differentiate into any foetal or adult cell types. The procurement of such cells is, however, highly limited and constantly subjected to severe ethical concerns since natural pluripotent stem cells are from embryonic origin and thus can only be obtained from an embryo. Therefore, intensive research efforts have been devoted to uncover alternative non-embryonic sources of pluripotent stem cells that are free of ethical concerns.

A breakthrough discovery revealed that non-embryonic stem cells (also referred to as adult stem cells or somatic stem cells) exist in almost all adult tissues of the body. Examples of non-embryonic stem cells include, mesenchymal stem cells, hematopoietic stem cells, epithelial stem cells, dermal stem cells, and neural stem cells, hair follicular stem cells, and others. In contrast to embryonic stem cells, non-embryonic stem cells are multipotent rather than pluripotent. Multipotent stem cells have the potential to give rise to cells from multiple lineages, but not all lineages. In other words, non-embryonic stem cells cannot naturally differentiate into any type of cells, at least not without undergoing artificial manipulations. Indeed, it was discovered that multipotent non-embryonic stem cells can be artificially induced to become pluripotent in laboratory settings by inducing the forced expression of certain genes. Such artificially transformed cells are also referred to as "induced pluripotent stem cell". However, the use of induced pluripotent stem cells is controversial since such cells are often highly tumorigenic.

Another breakthrough discovery revealed that not only do hair follicular stem cells appear to escape the tumorigenic fate but they also display a high proliferative and clonigenic ability while having the potential to differentiate, however, under artificial conditions, in a variety of different tissues including neural tissue, eye tissue (e.g. retinal pigment epithelium tissue), heart tissue (e.g. cardiomyocytes), tooth tissue, adipogenic tissue, chondrogenic tissue, osteogenic tissue, and myogenic lineages similar to bone marrow, and others. Therefore, because of their broad regenerative potential, great accessibility, and non-oncogenic quality, hair follicular stem cells are currently considered one of the most promising sources of non-embryonic stem cells for the purpose of tissue engineering, tissue transplantation technology, facial and body rejuvenation technology, and other cosmetic technologies as well as therapeutic procedures (e.g. regenerative medicine).

Another rapidly developing field is the field of "autologous products" and related cosmetic treatments and therapeutic procedures, which is based on the principle of taking a subject's own proteins, cells, or tissues and reintroduce them back into the same subject. Such technology is particularly advantageous in the fields of cosmetic tissue engineering, tissue transplantation technology and facial and body rejuvenation technology, therapeutic procedures (e.g. regenerative medicine) and others, since it prevents the occurrence of complications related to immune rejection and/or infection. Therefore, the interest in hair follicular stem cells, especially from autologous sources, is currently heightened, particularly for developing improved methods for efficiently manipulating hair follicular stem cells in vitro. Specifically, because the number of hair follicular stem cells that can be harvested from donor hairs is relatively little compared to the large amount of hair follicular stem cells needed, for instance, in cosmetic tissue engineering, tissue transplantation technology and facial and body rejuvenation technology, therapeutic procedures (e.g. regenerative medicine) and others, there is a growing need for improved in vitro methods for culturing and expanding (multiplying their number or boosting proliferation) hair follicular stem cells. In parallel, there is also a great need for improved in vitro methods and compositions for generating desired cell types and/or tissue types from hair follicular stem cells, particularly those issued from in vitro culture. More precisely, there is great need for improved cell-specific or tissue-specific compositions, in particular autologous cell-specific or tissue-specific compositions, that enable hair follicular stem cells to proliferate and differentiate in a desired cell type and/or tissue type in a more efficient manner.

Generally, differentiation media for mesenchymal stem cells such as hair follicle stem cells comprise Foetal Bovine Serum. Serum is a major source of viral contaminants which, once present, are difficult to remove from cultures. It can contain viruses, prions and *mycoplasma*, which may skew the outcome of scientific experiments and may transfer diseases to cultured cell. Additionally, considerable ethical debate surrounds the production of Foetal Bovine Serum. In the art there is a need for proliferation and differentiation media devoid of Foetal Bovine Serum.

SUMMARY OF THE INVENTION

In a first aspect, the present invention relates to a composition for generating a desired cell type and/or tissue type from at least one hair follicular stem cell, said composition comprising at least one anti-apoptotic compound, wherein said anti-apoptotic agent is a physiologically acceptable vanadium compound, at least one anti-oxidant compound, at least one stem cell enhancer compound, at least one extracellular matrix compound, and at least one differentiation inducing factor.

The physiologically acceptable vanadium compound may be selected from the group consisting of bis (maltolato) oxovanadium, oxovanadium, and orthovanadium, and is preferably bis (maltolato) oxovanadium.

One or more second or further anti-apoptotic compounds selected from the group of a triiodothyronine, estradiol, progesterone, tissue extract, insulin, transferrin, selenium, L-cysteine, adenosine triphosphate-magnesium chloride, and L-leucine may further be included in the composition taught herein.

The tissue extract may be bovine pituitary extract.

In an embodiment, the anti-oxidant compound is selected from the group of quercetin, monohydroxyethyl rutoside, vitamin C, lipoic acid, deferoxamine mesylate, and vitamin E, preferably from quercetin and mono-hydroxyethyl rutoside.

In an embodiment, the stem cell enhancer compound is selected from the group consisting of erythropoietin, CD34-positive cell, and retinoic acid, preferably from the group of erythropoietin and CD34-positive cell. In a suitable embodiment, the stem cell enhancer compound is erythropoietin.

The erythropoietin and/or the CD34-positive cell may be derived from peripheral blood or bone marrow of a donor subject. The CD34-positive cell is obtainable or obtained from a CD34-positive cell line, e.g., a human CD34-positive cell line.

The composition taught herein may further comprise at least one degranulating agent, e.g., Compound 48/80.

The composition taught herein may further comprise an inorganic salt, such as $CaCl_2$.

In an embodiment, the extracellular matrix compound is selected from the group of: platelet rich plasma, laminin, collagen IV, heparan sulfate, entactin, and chondroitin sulfate.

In an embodiment, the extracellular matrix compound is platelet rich plasma, which may be derived from peripheral blood of a donor subject.

The composition taught herein may further comprise one or more ingredients selected from the group of albumin, essential and non-essential amino acids, vitamins, trace elements, organic constituents, growth supplement, and antibiotics.

The desired cell type may be selected from the group of nerve cell, photoreceptor cell, cardiomyocyte, odontoblast, epithelial cell, keratinocyte cell, fibroblast cell, fat cell, blood cell, immune cell, muscle cell, skin cell, hair follicular cell, osteoblast, osteocyte, osteoclast, and chondrocyte.

The desired tissue type may be selected from the group of neural tissue, eye tissue, heart tissue, tooth tissue, epithelial tissue, keratinocyte tissue, fibroblast tissue, connective tissue, fat tissue, muscle tissue, skin tissue, hair tissue, bone tissue, and cartilage tissue.

The differentiation inducing factor may be selected from the group consisting of basic fibroblast growth factor, insulin-growth factor, epidermal growth factor, transforming growth factor, nerve growth factor, fibroblast growth factor, epithelial growth factor, taurin, activin A, and 5-azacytidine.

The insulin-like growth factor may selected from the group consisting of insulin-like growth factor type 1 and insulin-like growth factor type 2.

The differentiation inducing factor may epidermal growth factor, and said desired cell type and/or tissue type is epidermal cell and/or tissue type, skin cell and/or tissue type, blood vessel cell and/or tissue type, or bone cell and/or tissue type. The epidermal growth factor may be selected from the group consisting of: heparan-binding epidermal growth-like growth factor, epiregulin, epigen, betacellulin, neuregulin-1, neuregulin-2, neuregulin-3, and neuregulin-4.

The differentiation inducing factor may be transforming growth factor, and said desired cell type and/or tissue type is cartilage cell and/or tissue type, heart valve cell and/or tissue type, and skeletal muscle cell and/or tissue type. The transforming growth factor may be selected from the group consisting of: transforming growth factor alpha and transforming growth factor beta.

The differentiation inducing factor is selected from activin A, taurin, and epidermal growth factor, and said desired cell type and/or tissue type is photoreceptor cell and/or retinal tissue.

The differentiation inducing factor may be fibroblast growth factor, and said desired cell type and/or tissue type is fibroblast cell, skin cell and/or skin tissue, or blood vessel cell and/or blood vessel tissue.

The differentiation inducing factor may be epithelial growth factor, and said desired cell type and/or tissue type is keratinocyte cell and/or keratinocyte tissue.

The composition taught herein may further comprise a serum free growth medium.

In another aspect, the present invention provides an in vitro method for generating a desired cell type and/or tissue type from at least one hair follicular stem cell, said method comprising the steps of:
  providing at least one hair follicular stem cell;
  culturing the at least one hair follicular stem cell in a medium so as to obtain a population of hair follicular stem cells;
  contacting the population of hair follicular stem cells of step (b) with a composition taught herein and allowing said population of hair follicular stem cells to differentiate into the desired cell type and/or tissue type under conditions favorable for differentiation; and
  harvesting the desired cell type and/or tissue type.

The at least one hair follicular stem cell of step (a) may be obtained from at least a part of a hair follicle in the anagen phase. The at least a part of a hair follicle in the anagen phase may have been obtained by plucking a hair from a donor area of a subject.

The at least a part of a hair follicle may be contacted with a medium comprising collagenase IV.

The hair follicular stem cell is preferably a human hair follicular stem cell.

The medium is preferably a serum-free growth medium, optionally further supplemented with at least one tissue extract, e.g., a bovine pituitary extract compound.

The desired cell type and/or tissue type is preferably intended for introduction in a recipient region in a subject, and wherein the at least one hair follicular stem cell of step (a) is derived from said subject, and wherein the composition of step (c) comprises at least one CD34-positive cell derived from said subject and/or platelet rich plasma derived from said subject.

In another aspect, the present invention relates to use of a desired cell type and/or tissue type obtainable or obtained by the in vitro method taught herein for a cosmetic purpose.

The invention also relates to use of a desired cell type and/or tissue type obtainable by the in vitro method taught herein for cosmetic tissue repair and/or wound healing.

The invention further pertains to use of a desired cell type and/or tissue type obtainable by the in vitro method taught herein for cosmetic facial and body rejuvenation.

The invention further provides use of a desired cell type and/or tissue type obtainable by the in vitro method taught herein for regenerative medicine.

Finally, the present invention relates to a kit comprising the composition taught herein, optionally with a leaflet comprising written information on how to use the composition taught herein to generate a desired cell and/or tissue type.

DETAILED DESCRIPTION OF THE INVENTION

General Definitions

The term 'anti-apoptotic compound' as used herein refers to a compound capable of preventing or reducing apoptosis. The term 'anti-apoptotic compound' is commonly used by the skilled person to describe compounds or substances having anti-apoptotic activity. Non-limiting examples of anti-apoptotic compounds include: physiologically acceptable vanadium compounds (e.g. bis (maltolato) oxovanadium, oxovanadium, orthovanadium), triodothyronine, estradiol, progesterone, insulin, transferrin, selenium, L-cysteine, L-leucine, adenosine triphosphate-magnesium chloride, tissue extract (e.g. bovine pituitary extract), and others.

The term 'anti-oxidant compound' as used herein refers to a compound capable of inhibiting or reducing the oxidation of other molecules and/or counteracting the effects of oxidative stress in a cell and/or tissue. The skilled person is well acquainted with the meaning of the term 'anti-oxidant' and recognizes it as well-known category of compounds used in various compositions or products. Non-limiting examples of anti-oxidant include: quercetin, monohydroxyethyl rutoside, vitamin C, lipoic acid, deferoxamine mesylate, vitamin E, and others.

The term 'stem-cell enhancer compound' as used herein, refers to a compound capable of enhancing the reprogramming of a stem cell or differentiation of a stem cell into a desired tissue type. Stem-cell enhancer compounds are also commonly used to promote expansion of stem cells while maintaining their genomic stability and viability under culture conditions. The skilled person is well acquainted with the term 'stem-cell enhancer compound' particularly in the context of regenerative medicine and cosmetic procedures, where stem cells are used to generate various types of tissues in vitro. Non-limiting examples of stem-cell enhancer compounds include erythropoietin, CD34-positive cells, retinoic acid and others.

The term "CD34-positive cell" refers to a cell positive for the molecular marker CD34, which is a surface glycoprotein functioning as a cell-cell adhesion factor. CD34 may also mediate the attachment of stem cells to bone marrow extracellular matrix or directly to stromal cells. CD34 is also the name for the human gene that encodes the protein. CD34 represents a well-known marker for primitive blood- and bone marrow-derived progenitor cells, especially for hematopoietic and endothelial progenitors. CD34-positive cells may be isolated from peripheral blood or bone marrow in a subject. It is particularly advantageous to isolate CD34-positive cells from peripheral blood or bone marrow of a patient in the context where an autologous tissue graft is desired, for instance. CD34-positive cells is one example of a stem cell enhancer compound.

The term 'extracellular matrix compound' as used herein refers to a compound capable of providing structural and biochemical support to the cells in a tissue or agglomerate of cells in in vivo and in vitro (e.g. culture) contexts. Extracellular matrix compounds are also widely known to promote cell adhesion, cell-to-cell communication and differentiation within a given tissue or agglomerate of cells in a culture medium. The skilled person is familiar with the term 'extracellular matrix compound' and recognizes that the term 'extracellular matrix compound' encompasses a wide variety of compounds useful in the context of cellular or tissue culture. Non-limiting examples of extracellular matrix compounds include platelet rich plasma, laminin, collagene IV, heparan sulphate, entactin, chondroitin sulphate, and the likes.

The term "differentiation inducing factor" as used herein refers to a compound that is capable of inducing differentiation of a mesenchymal stem cell, such as a hair follicular stem cell, into a different, desired, cell type, such as neural cell, photoreceptor cell, cardiomyocytes, smooth muscle cells, epithelial cells, and the like. A differentiation inducing factor may be any type of compound. For example, a differentiation inducing factor may be a well-known growth factors or any other chemical compound. In order to induce differentiation, differentiation inducing factors may be used in combination.

The term "growth factor" as used herein refers to a naturally occurring substance capable of stimulating cellular growth, proliferation, cellular differentiation, and/or cellular maturation. Growth factors exist in the form of either proteins or steroid hormones. Growth factors are important for regulating a variety of cellular processes. Growth factors typically act as signaling molecules between cells. However, their ability to promote cellular growth, proliferation, cellular differentiation, and cellular maturation varies between growth factors. A non-limiting list of examples of growth factors includes: basic fibroblast growth factor. adrenomedullin, angiopoietin, autocrine motility factor, bone morphogenetic proteins, brain-derived neurotrophic factor, epidermal growth factor, epithelial growth factor, fibroblast growth factor, glial cell line-derived neurotrophic factor, granulocyte colony-stimulating factor, granulocyte macrophage colony-stimulating factor, growth differentiation factor-9, hepatocyte growth factor, hepatoma-derived growth factor, insulin growth factor, insulin-like growth factor, migration-stimulating factor, myostatin, nerve growth factor, and other neurotrophins, platelet-derived growth factor, transforming growth factor alpha, transforming growth factor beta, tumor-necrosis-factor-alpha, vascular endothelial growth factor, placental growth factor, fetal bovine somatotrophin, and cytokines (e.g. IL-1-cofactor for IL-3 and IL-6, IL-2-t-cell growth factor, IL-3, IL-4, IL-5, IL-6, and IL-7).

As used herein, the term "hair follicular stem cells" may include hair follicle epithelial stem cells, hair follicle mesenchymal-like stem cells, hair follicle melanocyte stem cells, and/or nestin-positive stem cells.

The terms "neural cells and/or neural tissue" and "nerve cell and/or nerve tissue" as used herein refer to cell and/or tissue having origin from the main component of the two parts of the nervous system; the brain and spinal cord of the central nervous system (CNS), and the branching peripheral nerves of the peripheral nervous system (PNS). The term "nervous cell and/or tissue" is also commonly used as an equivalent to "neural cells and/or neural tissue" and "nerve cell and/or nerve tissue". In the present invention, these terms are used interchangeably.

The terms "autologous" in the context of the present invention means "derived or transferred from the same individual's body", and may refer to organs, tissues, cells, fluids, or proteins a subject, and which are to be administered to or transplanted in (optionally, another part of the body) the same individual. Organs, tissue, cells, or proteins transplanted by such "autologous" procedure is referred to as an autograft or autotransplant.

The term "allogeneic" as used herein, refers to organs, tissues, cells, fluids or proteins taken from a donor subject, and which are to be administered to or transplanted in a recipient subject of the same species that is genetically non-identical to the donor subject. Organs, tissue, cells, fluids or proteins transplanted by such "allogeneic" procedure is referred to as an allograft or allotransplant.

The term "hair follicle" refers to a mammalian skin organ that produces hair. More particularly, the hair follicle is composed of the dermal papilla (DP), dermal sheath (DS), outer root sheath (ORS), inner root sheath (IRS), and hair shaft. The upper and lower parts of the hair follicle both comprise hair follicular stem cells that are capable of generating a new hair. These are referred to as 'bulge stem cells' and 'matrix stem cells', respectively.

The term "at least a part of a hair follicle" as used herein refers to a part of a hair follicle or an entire hair follicle. The at least a part of a hair follicle comprises at least one hair follicular stem cell, but preferably more than one. The hair follicular stem cells may be either bulge stem cells or matrix stem cells, or both. Preferably, the hair follicular stem cells comprise at least bulge stem cells or derivatives thereof.

The terms "anagen phase", "catagen phase", and "telogen phase" represent the three phases of the natural growth cycle of the hair, including the growth phase, the transitional phase (also referred to as involuting or regressing phase), and the death phase (also referred to as resting or quiescent phase), respectively.

The term "three dimensional culture" refers to a method of culturing cells wherein cells are implanted or seeded into an artificial structure capable of supporting three-dimensional tissue formation. These structures, typically called scaffolds, are critical, both ex vivo as well as in vivo, to recapitulating the in vivo milieu and allowing cells to influence their own microenvironments.

The term "expanding" or the term "multiplying" as used herein refer to the proliferation of one cell to two cells, and so on. During the process of hair follicular stem cell expansion or multiplication, a hair follicular stem cell is self-renewing. Self-renewal of a cell is the ability of a given cell to go through numerous cycles of cell division while maintaining an undifferentiated state, i.e. the hair follicular stem cell remains a hair follicular stem cell regardless of the number of cell division cycles.

COMPOSITIONS OF THE INVENTION

In a first aspect, the present invention relates to a composition that is suitable for generating a desired cell type and/or tissue type from at least one hair follicular stem cell, i.e., for differentiating said hair follicular stem cell into a different cell type, said composition comprising at least one anti-apoptotic compound, wherein said anti-apoptotic agent is a physiologically acceptable vanadium compound, at least one anti-oxidant compound, at least one stem cell enhancer compound, at least one extracellular matrix compound, and at least one differentiation inducing factor. The composition taught herein may be devoid of the Foetal Bovine Serum (FBS) that is commonly used in culturing and differentiating of cells and is therefore suitable for culture of cells and tissues that are intended to be re-applied into or onto the human body.

Anti-apoptotic compounds, anti-oxidant compounds, stem cell enhancer compounds, extracellular matrix compounds, and differentiation inducing factors are well-known in the art and may even be commercially available. Any commercially available anti-apoptotic compounds, anti-oxidant compounds, stem cell enhancer compounds, extracellular matrix compounds, and differentiation inducing factors may be used for preparing the composition of the present invention.

In an embodiment, the physiologically acceptable vanadium compound is selected from the group consisting of bis (maltolato) oxovanadium (Cas no. 38213-69-3), oxovanadium, orthovanadium and derivatives thereof. In a more preferred embodiment, the physiologically acceptable vanadium compound is Bis (maltolato) oxovanadium. Any physiologically acceptable concentrations (mg/ml) of Bis (maltolato) oxovanadium can be used in the composition of the present invention. However, a concentration of 0.01-100 mg/ml, more preferably 0.1-10 mg/ml, more preferably 0.5-8 mg/ml, more preferably 0.6-6 mg/ml, more preferably 0.7-3 mg/ml, 0.8-2 mg/ml, more preferably 0.9-1.5 mg/ml, more preferably about 1 mg/ml of Bis (maltolato) oxovanadium is preferred in the present invention. The present inventor has found that the use of an anti-apoptotic compound such as a physiologically acceptable vanadium compound, especially Bis (maltolato) oxovanadium, was particularly effective relative to other types of anti-apoptotic agents. Specifically, it was found that the incorporation of a physiologically acceptable vanadium compound, especially Bis (maltolato) oxovanadium, into the composition greatly boosted the efficiency of other ingredients present in the compositions of the present invention such as growth factors.

In one embodiment, Bis (maltolato) oxovanadium, oxovanadium and orthovanadium may be used interchangeably.

In one embodiment, the composition as taught herein may further comprise a second or further anti-apoptotic agents selected from the group consisting of triodothyronine, estradiol, progesterone, insulin, transferrin, selenium, L-cysteine, L-leucine, adenosine triphosphate-magnesium chloride, and tissue extract.

Tissue extracts are well-known in the art and are commercially available. Methods and protocols for preparing tissue extracts are also well-known in the art. Any tissue commercially available or home-made extracts can be used to prepare the composition of the invention but bovine pituitary extract is preferred. It may be particularly advantageous to incorporate a tissue extract, particularly a bovine pituitary extract, into the composition of the invention for the purpose of maintaining the hair follicular stem cells in an undifferentiated state. The maintenance of hair follicular stem cells into an undifferentiated state is important for instance during the culture and expansion (or multiplication) phases, so that the hair follicular stem cells can undergo self-renewal, i.e. go through numerous cycles of cell division, while maintaining an undifferentiated state (maintain genetic stability). This process is typically performed to increase the population of hair follicular stem cells prior to using said population of hair follicular stem cells for generating a desired cell type and/or tissue type.

In an embodiment, at least two, three, four, five, six, seven, eight, nine, ten, or more second or further anti-apoptotic compounds selected from the group of: triodothyronine, estradiol, progesterone, tissue extract (e.g. bovine pituitary extract), insulin, transferrin, selenium, L-cysteine, adenosine triphosphate-magnesium chloride, and L-leucine are present in the composition of the invention. Specifically it was found by the present inventor that the incorporation of at least two, preferably three, preferably four, preferably five, preferably six, preferably seven, preferably eight, preferably nine, and more preferably ten, was particularly advantageous since it further improved the efficiency of the composition of the invention, relative to a composition where only the physiologically acceptable vanadium compound is present.

In an embodiment, the anti-oxidant compound of the composition of the invention is selected from the group of quercetin, monohydroxyethyl rutoside, vitamin C, deferoxamine mesylate, vitamin E, and lipoic acid, and a derivative thereof. Anti-oxidant compounds are well-known in the art and are commercially available. Any commercially available anti-oxidant compounds can be used in the present invention. However, in an embodiment, the incorporation of a flavonoid such as quercetin or mono-hydroxyethyl rutoside, particularly mono-hydroxyethyl rutoside, is preferred. Any physiologically acceptable concentrations (mg/ml) of mono-hydroxyethyl rutoside that have anti-oxidant activity can be used in the composition of the present invention. For example, the concentration may be in the range of 0.0025-25 mg/ml, more preferably 0.025-2.5 mg/ml, more preferably 0.12-2 mg/ml, more preferably 0.15-1.5 mg/ml, more preferably 0.18-1 mg/ml, more preferably 0.2-0.5 mg/ml, more preferably 0.21-0.4 mg/ml, more preferably 0.23-0.3 mg/ml, more preferably 0.23-0.28 mg/ml, and more preferably is about 0.25 mg/ml of mono-hydroxyethyl rutoside.

In another embodiment, at least two, three, or more anti-oxidant compounds selected from the group of: quercetin, monohydroxyethyl rutoside, vitamin C, deferoxamine mesylate, vitamin E, and lipoic acid are incorporated in the composition of the invention. It was found by the inventor that the presence of more than two anti-oxidant compounds, preferably three or more anti-oxidant compounds, further improved the effectiveness of the composition of the invention, relative to a composition where only one anti-oxidant compound is present.

In an embodiment, the at least one stem cell enhancer compound of the composition of the invention is selected from the group of erythropoietin, CD34-positive cell, and retinoic acid. In an embodiment, the stem cell enhancer is selected from the group consisting of erythropoietin and CD34-positive cell. Particularly erythropoietin was found to be very effective.

In another preferred embodiment, the stem cell enhancer compound is a CD34-positive cell. Any physiologically acceptable amounts (cells/ml) of CD34-positive cells can be used in the present invention but an amount of about $1 \times 10^1$-$1 \times 10^5$ cells/ml, more preferably about $1 \times 10^2$-$1 \times 10^4$ cells/ml, more preferably about $5 \times 10^2$-$1 \times 10^4$ cells/ml, more preferably about $5 \times 10^2$-$0.5 \times 10^4$ cells/ml, more preferably about $6 \times 10^2$-$0.4 \times 10^4$ cells/ml, more preferably about $7 \times 10^2$-$0.3 \times 10^4$ cells/ml, more preferably about $8 \times 10^2$-$0.2 \times 10^4$ cells/ml, more preferably about $9 \times 10^2$-$0.15 \times 10^4$ cells/ml, more preferably about $1 \times 10^3$ CD34-positive cells/ml is preferred. In an embodiment, the CD34-positive cell is obtainable or obtained from a CD34-positive cell line. CD34-positive cell lines are known in the art and are commercially available, for instance KG-1a, KG-1, and NIH3T3. In an embodiment, the CD34-positive cell is obtainable or obtained from a human CD34-positive cell line, which are also commercially available such as KG-1a, KG-1 and NIH3T3. However, in a further preferred embodiment, the CD34-positive cell is derived from the peripheral blood or from the bone marrow of a donor subject. Examples of a donor subject include a non-human mammal subject or a human subject. In a further preferred embodiment, the donor subject is a human subject. Methods for isolating and identifying CD34-positive cells from the peripheral blood or bone marrow are known in the art. For instance, immunohistochemical methods and kits comprising antibodies directed against the CD34 antigen can be used to identify CD34-positive cells.

In a more preferred embodiment, the stem cell enhancer compound is erythropoietin. Any physiologically acceptable amounts of erythropoietin can be used in the present invention but an amount of about 0.1 unit to 10 units of erythropoietin/ml is used, preferably about 0.3 unit to 8 units of erythropoietin/ml is used, preferably about 0.5 unit to 6 units of erythropoietin/ml is used, about 0.7 unit to 4 units of erythropoietin/ml is used, about 0.9 unit to 2 units of erythropoietin/ml is used, about 0.95 unit to 1.5 units of erythropoietin/ml is used, more preferably about 1 unit of erythropoietin/ml is used. In an embodiment, erythropoietin may be obtained from a commercial source. In a preferred embodiment, erythropoietin may be obtained from a donor subject, for instance from the blood circulation or from bone marrow of a donor subject. Examples of a donor subject include a non-human mammal subject or a human subject. In a further preferred embodiment, the donor subject is a human subject. Methods for obtaining erythropoietin from the peripheral blood or bone marrow are known in the art. The person skilled in the art is well acquainted with the term "Unit" (abbreviated as "U") as a measure unit for amount of erythropoietin. Erythropoietin amounts are expressed in units (U) rather than in grams or moles, because native erythropoietin and recombinant human erythropoietin are mixtures of isoforms with differing bioactivities. In the present invention, one unit is defined as the amount of erythropoietin that is required to produce equivalent $^3$[H]-thymidine incorporation into spleen cells from phenylhydrazine treated mice to that expressed of 1 unit of the WHO-erythropoietin reference standard ($2^{nd}$ First International Reference Preparation).

In an embodiment, at least two, three or more stem cell enhancer compounds selected from the group of erythropoietin, CD34-positive cell, and retinoic acid, are present in the composition of the invention. It was found by the present inventor that the presence of at least two stem cell enhancer compounds, preferably the presence of three stem cell enhancer compounds, selected from the group of: erythropoietin, CD34-positive cell, and retinoic acid, led to an increase in the efficiency of the composition of the invention, relative to a composition wherein only one stem cell enhancer compound is present.

In a further embodiment, the composition of the invention may comprise at least one degranulating agent. In an embodiment the degranulating agent is Compound 48/80. Degranulating agents, such as Compound 48/80, are known in the art and are commercially available. In another embodiment, the composition of the invention may also comprise at least one inorganic salt. Said inorganic salt may aid in optimizing the action of the degranulating agent. Inorganic salts are known in the art and are also commercially available. In an embodiment the inorganic salt is $CaCl_2$. It may be particularly advantageous to incorporate at least one degranulating agent such as Compound 48/80 and at least one inorganic salt such $CaCl_2$ in a composition of the invention comprising a CD34-positive cell.

In an embodiment, the at least one extracellular matrix compound is selected from the group of: platelet rich plasma, laminin, collagen IV, heparan sulfate, entactin, and chondroitin sulfate. The term "extracellular matrix compound" is a term well-known to those skilled in the art. Non-limiting examples of extracellular matrix compounds are collagen, laminin, elastin, fibronectin, and the like, which are widely commercially available. Substitutes thereof are also known in the art and are commercially available. Methods and protocols to prepare extracellular matrix compounds are also known in the art. Any homemade or commercially available extracellular compounds can be used in the composition of the invention. In a preferred embodiment, the extracellular matrix compound is platelet rich plasma. Any physiologically acceptable concentrations (ml/ml) of platelet rich plasma can be used in the present invention but a concentration in the range of about 0.0005-5 ml/ml, more preferably about 0.005-0.5 ml/ml, more preferably about 0.01-0.25 ml/ml, more preferably about 0.02-0.15 ml/ml, more preferably about 0.03-0.10 ml/ml, more preferably about 0.04-0.08 ml/ml, more preferably about 0.045-0.06 ml/ml, more preferably about 0.05 ml/ml of platelet rich plasma is preferred. In one embodiment, the platelet rich plasma is derived from the peripheral blood of a donor subject, preferably a human subject. Protocols and methods to obtain platelet rich plasma from the blood of a subject are known in the art.

In an embodiment, at least two, three, four, five, six, or more, extracellular matrix compounds selected from the group of: platelet rich plasma, laminin, collagen IV, heparan sulfate, entactin, and chondroitin sulfate, are present in the composition of the invention. It was found by the present inventor that the incorporation of at least two, preferably three, preferably four, preferably five, more preferably six extracellular matrix compounds into the composition of the invention, led to an increase in the effectiveness of the composition of the invention, relative to composition wherein only one extracellular matrix compound is present.

In another embodiment, the composition of the invention may optionally further comprise one or more ingredients selected from the group of: albumin, essential and non-essential amino acids, vitamins, trace elements, organic constituents, inorganic salts, growth supplement, and antibiotics. It may be advantageous to add one or more of said ingredients to further promote growth and proliferation of hair follicular stem cells while circumventing bacterial contamination in the culture medium.

In an embodiment, the composition taught herein does not comprise Foetal Bovine Serum (also known as Foetal Calf Serum), or any animal serum, including human serum, unless the serum is autologous to the subject to which a desired cell type or a desired tissue type is transplanted. For example, the desired cell type generated using the composition of the invention may be transplanted into a subject, who may have also provided the hair follicular stem cell.

In a highly suitable embodiment, the composition of the invention comprises Bis (maltolato) oxovanadium in a concentration in the range of 0.01-100 mg/ml, more preferably 0.1-10 mg/ml, more preferably 0.5-8 mg/ml, more preferably 0.6-6 mg/ml, more preferably 0.7-3 mg/ml, 0.8-2 mg/ml, more preferably 0.9-1.5 mg/ml, more preferably about 1 mg/ml; erythropoietin in an amount of about 0.1 unit to 10 units/ml, preferably about 0.3 unit to 8 units/ml, more preferably about 0.5 unit to 6 units/ml, even more preferably about 0.7 unit to 4 units/ml, yet more preferably about 0.9 unit to 2 units/ml, even more preferably about 0.95 unit to 1.5 units of erythropoietin/ml; at least one antioxidant compound, preferably selected from the group of quercetin, monohydroxyethyl rutoside, vitamin C, deferoxamine mesylate, vitamin E, and lipoic acid, or any combination thereof, e.g., a combination of monohydroxyethyl rutoside, vitamin E and lipoic acid; at least one extracellular matrix compound, e.g., platelet rich plasma; and at least one differentiation inducing factor.

The differentiation inducing factor may be selected from the group consisting of: growth factors, such basic fibroblast growth factor, nerve growth factor, insulin-growth factor, epidermal growth factor, transforming growth factor, and epithelial growth factor; 5-azacytidine; activin A; taurin; and any combination thereof. Other non-limiting examples of growth factors from which the growth factor may be selected include: adrenomedullin, angiopoietin, autocrine motility factor, bone morphogenetic proteins, brain-derived neurotrophic factor, glial cell line-derived neurotrophic factor, granulocyte colony-stimulating factor, granulocyte macrophage colony-stimulating factor, growth differentiation factor-9, hepatocyte growth factor, hepatoma-derived growth factor, insulin-like growth factor, migration-stimulating factor, myostatin, neurotrophins, platelet-derived growth factor, transforming growth factor alpha, transforming growth factor beta, tumor-necrosis-factor-alpha, vascular endothelial growth factor, placental growth factor, fetal bovine somatotrophin, and cytokines (e.g. IL-1-cofactor for IL-3 and IL-6, IL-2-t-cell growth factor, IL-3, IL-4, IL-5, IL-6, and IL-7). Any physiologically acceptable concentration (ng/ml) of growth factor may be used in the present invention but a concentration in the range of about 0.01-100000 ng/ml, more preferably about 0.1-10000 ng/ml, more preferably about 1-1000 ng/ml, more preferably about 10-500 ng/ml, more preferably about 50-400 ng/ml, more preferably about 70-300 ng/ml, more preferably about 80-200 ng/ml, more preferably about 90-150 ng/ml, more preferably about 95-125 ng/ml of growth factor is preferred.

In an embodiment, the growth factor may be selected from one or more of basic fibroblast growth factor, insulin-like growth factor and nerve growth factor, and the desired cell type and/or tissue type is neural cell and/or neural tissue.

In an embodiment, the differentiation inducing factors used are the growth factors vascular endothelial growth factor (VEGF) and basic fibroblast growth factor (bFGF), and the desired cell type is cells of an endothelial lineage (Xu et al. Mol Med Rep. 2014, vol. 9:204-210). VEGF may be used in a contraction in the range of about 0.1-10,000 ng/ml, more preferably about 1-1,000 ng/ml, more preferably about 10-500 ng/ml, more preferably about 25-200 ng/ml, more preferably about 30-100 ng/ml. bFGF may be used in a concentration of about 0.01-10,000 ng/ml, more preferably about 0.1-1,000 ng/ml, more preferably about 0.5-200 ng/ml, more preferably about 1-100 ng/ml, more preferably about 5-50 ng/ml.

In another embodiment, the differentiation inducing factors used are transforming growth factor-$\beta 1$ (TGF-$\beta 1$) and platelet-derived growth factor BB (PDGF-BB), and the desired cell type is contractile smooth muscle cells (Xu et al. Mol Med Rep. 2013, vol. 8:1715-1721). TGF-$\beta 1$ may be employed in a concentration of about 0.01-10,000 ng/ml, more preferably about 0.1-1,000 ng/ml, more preferably about 0.5-200 ng/ml, more preferably about 1-100 ng/ml, more preferably about 2-50 ng/ml. PDGF-BB may be employed in a concentration of about 0.01-10,000 ng/ml, more preferably about 0.1-1,000 ng/ml, more preferably about 0.5-200 ng/ml, more preferably about 1-100 ng/ml, more preferably about 2-50 ng/ml.

In one embodiment, the differentiation inducing factors are selected from taurine, activin A and epidermal growth factor (EGF), or a combination thereof, and the desired cell type is a photoreceptor cell (cells expressing photoreceptor-specific markers rhodopsin, opsin and recoverin), and/or tissue type is retinal tissue, e.g., retinal pigment epithelium tissue (Kicic et al. 2003. J. Neurosci. Vol. 23:7742-7749). The obtained cells may be transplanted into the eye to counteract eye degenerations, such as macular degeneration, e.g., age-related macular degeneration. Taurin may be employed in a concentration in the range of 0.1-1,000 µM, preferably 1-500 µM, more preferably 5-100 µM, most preferably 25-50 µM. Activin A may be employed in a concentration in the range of 0.1-10,000 ng/ml, preferably 1-1,000 ng/ml, more preferably 5-500 ng/ml, yet more preferably 10-300 ng/ml. even more preferably 50-200 ng/ml. Any physiologically acceptable concentration (ng/ml) of eptidermal growth factor may be used but a concentration in the range of about 0.1-100,000 ng/ml, more preferably about 1-10,000 ng/ml, more preferably about 10-1,000 ng/ml, more preferably about 50-500 ng/ml, more preferably about 60-400 ng/ml, more preferably about 70-300 ng/ml, more preferably about 80-200 ng/ml, more preferably about 90-150 ng/ml, more preferably about 95-125 ng/ml of epidermal growth factor is preferred.

In one embodiment, the differentiation inducing factor is 5-azacytidine and the desired cell type is a cardiomyocyte (Potdar and Prasannan. 2013. ISRN Stem cells. Article ID687282). The 5-azacytidine may be employed in a concentration in the range of 0.1-1,000 µM, preferably 1-500 µM, more preferably 5-100 µM, most preferably 5-50 µM.

In an embodiment, the growth factor is an epidermal growth factor and the desired cell type and/or tissue type is selected from the group consisting of epidermal cell and/or epidermal tissue, skin cell and/or skin tissue, blood vessel cell and/or blood vessel tissue, and bone cell and/or bone tissue. The epidermal growth factor may be selected from the group consisting of: heparan-binding epidermal growth-like growth factor, epiregulin, epigen, betacellulin, neuregulin-1, neuregulin-2, neuregulin-3, and neuregulin-4.

In an embodiment, the growth factor is transforming growth factor, and the desired cell type and/or tissue type is selected from the group consisting of cartilage cell and/or cartilage tissue, heart valve cell and/or heart valve tissue, and skeletal muscle cell and/or skeletal muscle tissue. The transforming growth factor may be selected from the group consisting of: transforming growth factor alpha and transforming growth factor beta.

In an embodiment, the growth factor is epithelial growth factor, and the desired cell type and/or tissue type is keratinocyte cell and/or keratinocyte tissue.

In an embodiment, the composition of the present invention further comprises a serum free growth medium. Serum free growth media are well-known in the art and are readily commercially available. The skilled person will know how to select an appropriate serum free growth medium. In preferred embodiment, the serum free growth medium further comprises at least one ingredient selected from the group of: albumin, sodium chloride, potassium chloride, magnesium sulphate, sodium phosphate, calcium chloride, glucose, sodium bicarbonate, sodium lactate, sodium pyruvate, human serum albumin, and insulin.

In vivo method for generating a desired cell type and/or tissue type from at least one hair follicular stem cell.

METHOD OF THE INVENTION

In a second aspect, the present invention relates to an improved in vivo method for generating a desired cell type and/or tissue type from at least one hair follicular stem cell, said method comprising the steps of:
(a) providing at least one hair follicular stem cell;
(b) culturing the at least one hair follicular stem cell in a serum-free growth medium so as to obtain a population of hair follicular stem cells;
(c) contacting the population of hair follicular stem cells of step (b) with a composition as taught herein and allowing said population of hair follicular stem cells to differentiate into the desired cell type and/or tissue type under conditions favourable for differentiation; and
(d) harvesting the desired cell type and/or tissue type.

In one embodiment, the at least one hair follicular stem cell of step (a) is obtained from at least a part of a hair follicle in the anagen phase. In another embodiment, the at least a part of a hair follicle in the anagen phase has been obtained by plucking the hair from a donor area of a subject. In a preferred embodiment, the donor subject is human. However, it is not essential that the hair follicular stem cell of step (a) be of human origin.

In step (a), the provision of at least a part of a hair follicle in the anagen phase can be performed by any methods known in the art, e.g. plucking one or more donor hairs from a donor subject, such as the scalp of a donor subject, and then selecting one or more donor hairs in the anagen phase. Selecting a donor hair in the anagen phase can be performed by a person with ordinary skill in the art. It is well known in the art that a hair in the anagen phase displays specific morphological and histological characteristics that distinguish it from a hair in another phase of the growth cycle, such as the catagen phase or telogen phase.

The hair may be plucked using any methods known in the art. For examples, the hair may be plucked using fingers or a plucking instrument (e.g. tweezers) may be used. In an embodiment, the donor hair is removed using a plucking instrument such as a hollow harvesting needle, as described in published international application WO2005077285.

In one embodiment, the at least a part of a hair follicle may be contacted with a medium comprising collagenase IV, in such a manner that at least one hair follicular stem cell is enzymatically dissociated from the at least part of a hair follicle in the anagen phase. It may be particularly advantageous to perform this step in a situation wherein the at least one hair follicular stem cell of step (a) is still attached or embedded within the hair follicle or part of a hair follicle. It is known in the art that hair follicular stem cells can be enzymatically dissociated from their respective hair follicle using enzymes such as collagenases. Collagenases, particularly collagenase IV, are well-known in the art and are commercially available. Protocols and methods for dissociating hair follicular stem cells using collagenases (e.g. collagenase IV) or other enzymes are also known and are used routinely in the art.

In step (a), in certain cases, e.g. when a mixed population of hair follicle cells is obtained from the hair follicle or part of a hair follicle, it may be advantageous to isolate and purify the hair follicular stem cells from the mixture, prior to conducting step (b). Methods and protocols for isolating, purifying, identifying, and separating hair follicular stem cells are known in the art.

In an embodiment, the at least one hair follicular stem cell of step (a) may be cultured and expanded in a serum-free growth medium of step (b) for at least two weeks, e.g., at least 3 weeks. Serum-free growth media are known in the art and are commercially available. Protocols and methods for preparing serum-free growth media are also known in the art. Any serum-free growth media can be used in the in vitro method of the invention. In a preferred embodiment, the serum-free growth medium of step (b) is further supplemented with at least one tissue extract, preferably a bovine pituitary extract. Without wishing to be bound by theory, it is hypothesized that the incorporation of a bovine pituitary extract actively blocks the hair follicular stem cells from undergoing differentiation during the culture and expansion phase of step (b). It In an embodiment, step (b) may be repeated for an additional at least two weeks, preferably at least 3 weeks in order to obtain an even greater expansion of the population of hair follicular stem cells.

In step (b), the at least one hair follicular stem cell of step (a) is cultured in such a manner that a population of hair follicular stem cells is obtained.

In step (b), in certain cases, for instance in case of the occurrence of cell death during the culturing period, it may be advantageous to remove dead cell from the culture environment. Protocols and methods to remove dead cells from a culture environment are known in the art. For instance, a gradient centrifugation method can be used to remove dead cells from the culture medium.

In step (b), it may be advantageous to replenish the culture medium of the step regularly, preferably on a daily basis (i.e. every 24 hours).

In step (b), it may also be particularly advantageous to culture the at least one hair follicular stem cell of step (a) in the context of a three-dimensional culture milieu. It is known in the art that three-dimensional cell culture systems allow various types of interactions to occur between the different cell types present in the culture in a manner that mimics what occurs in a natural environment. Methods and protocols for performing three-dimensional cell culture are also well known in the art.

In an embodiment, the serum-free growth medium of step (b) may further comprise one or more ingredients selected from the group of albumin, essential and non-essential amino acids, vitamins, trace elements, organic constituents, inorganic salts, growth supplement, hormones, antibiotics, and tissue extracts. The addition of one or more of said ingredients may be advantageous to further promote proliferation, expansion, and growth of the hair follicular stem cells while preventing bacterial contamination or eliminating other pathogens in the culture milieu.

In step (c), the population of hair follicular stem cells of step (b) is contacted with a composition as taught herein; and said population of hair follicular stem cells is allowed to differentiate into the desired cell type and/or tissue type under conditions favourable for differentiation.

In an embodiment, the population of hair follicular stem cells of step (b) is contacted with the composition of step (c) for at least two weeks, e.g., at least three weeks, at least four weeks, at least five weeks, at least six weeks, and the like. In an embodiment, the time period during which the population of hair follicular stem cells of step (b) is contacted with the medium of step (c) varies depending on the desired cell type and/or tissue type.

In another embodiment, the desired cell type of step (d) is selected from the group consisting of: neural cell, photoreceptor cell such as retinal pigment epithelium cell and rods and cones, heart cell such as cardiomyocyte and pacemaker cell, tooth cell such as odontoblast and other pulp cells, epithelial cell, keratinocyte cell, fibroblast cell, fat cell, blood cell, immune cell, muscle cell, skin cell, hair follicular stem cell, bone cell such as osteoblast, osteocyte, osteoclast, and cartilage cell such as chondrocyte. In a further embodiment, the desired tissue type of step (d) is selected from the group of: neural tissue, eye tissue, heart tissue, tooth tissue, epithelial tissue, keratinocyte tissue, connective tissue, fibroblast tissue, fat tissue, muscle tissue, skin tissue, hair tissue, bone tissue, and cartilage tissue.

In a preferred embodiment, the at least one hair follicular stem cell of step (a) is derived from a subject, and the composition of step (c) comprises at least one CD34-positive cell and/or platelet rich plasma derived from said subject, and wherein the desired cell type and/or tissue type of step (d) is introduced in a recipient region in said subject. In a more preferred embodiment, the composition of step (c) comprises erythropoietin and/or platelet rich plasma derived from said subject, and wherein the desired cell type and/or tissue type of step (d) is introduced in a recipient region in said subject.

It may be particularly advantageous that the at least one hair follicular stem cell of step (a) as well as one or more components of the composition of step (c) used to generate a desired cell type and/or tissue, are derived from the subject who will be receiving said newly generated desired cell type and/or tissue type. This is especially advantageous in the context wherein an autologous cell and/or tissue transplant into a subject is wanted. Overall, such procedure insures that (autologous) cell and/or tissue transplant or graft will be fully biologically compatible with the recipient subject without the occurrence of complications related to immune rejection and/or infection in said subject.

In an embodiment, steps (a), (b), (c), and (d) are performed under sterile conditions. Protocols and methods for manipulating, isolating identifying, purifying, culturing, maintaining, fertilizing, and harvesting cells, including hair follicular stem cells, are known in the art. It may be particularly advantageous to perform steps (a), (b), (c), and (d) under sterile conditions in the context where the new desired cell type and/or tissue type obtained in step (d) is used in cosmetic procedures in a subject, so as to avoid complications related to immune rejection and/or infection due to the presence of pathogens or other agents capable of causing an infection or immune rejection.

Suitable Uses of the Method and Composition of the Invention

In a third aspect, the present invention relates to the use of a desired cell type and/or tissue type obtainable or obtained by the in vitro method for generating a new cell type and/or tissue type from at least one hair follicular stem cell, as described herein, for a cosmetic and/or therapeutic purpose in a recipient subject. For instance, in one embodiment, the desired cell type and/or tissue type obtainable or obtained by the in vitro method of the present invention is used for cosmetic or therapeutic tissue repair and/or cosmetic or therapeutic wound healing in a subject, e.g. subjects experiencing loss of tissue (e.g. skin, fat, muscle, tendon, etc.) due to cell and/or tissue damage inflicted by a wound, a burn, a tear, a scar, acne, wrinkles, degeneration, diseases and/or aging. In a further embodiment, the desired cell type and/or tissue type obtainable or obtained by the in vitro method of the present invention, is used for cosmetic facial and body rejuvenation. For instance, the desired cell type and/or tissue type obtainable or obtained by the in vitro method of the present invention can be used to cosmetically reshape a certain part of the face and/or body of a subject, and/or to cosmetically modify (e.g. increase) the volume of a certain part of the face and/or body of a subject, and/or to cosmetically alter the texture of a certain part of the face and/or body of a subject.

In an embodiment, the desired cell type and/or tissue type obtainable or obtained by the in vitro method for generating a new cell type and/or tissue type from at least one hair follicular stem cell, as described herein, is used for therapeutic purposes, for instance regenerative medicine, in a recipient subject in need thereof. In one embodiment the desired cell type and/or tissue type obtainable or obtained by the in vitro method of the present invention can be used to repair, regenerate or replace damaged tissues or organs as well as lost tissues or organs, which occur as a result of degeneration and/or necrosis and/or apoptosis caused by aging, diseases, burns, accidents, injuries, cuts, ablations and the likes.

All publications cited herein are incorporated by reference.

BRIEF DESCRIPTION OF THE FIGURE RELATED TO THE INVENTION

FIG. 1 displays the effect of the physiologically acceptable vanadium compounds oxovanadium (OVAN) and bis (maltolato) oxovanadium (BMOV) on proliferation of keratinocytes. Proliferation of keratinocytes is expressed as the number of cells counted per amount of the culture milieu (i.e. number of cells×10E4/ml). The results reveal an enhanced proliferation of keratinocytes following treatment with a composition comprising a basic medium growth serum (SFK) supplemented with 1 mg/ml of OVAN or 1 mg/ml of BMOV relative to the control situation (i.e. basic growth medium (SFK) lacking a vanadium compound). Note that treatment with BMOV is associated with a greater number of proliferated cells relative to treatment with OVAN.

EXAMPLES

Example 1. Collection of Hair Follicular Stem Cells

Hair follicular stem cells were obtained from plucked hairs in the anagen phase, which were obtained from a donor subject, using a plucking instrument such as a hollow harvesting needle. Plucked hairs were inspected under a microscope. Plucked hairs not displaying the characteristics of a hair in the anagen phase were discarded.

Example 2. Pre-Treatment of Hair Follicular Stem Cells

Plucked hairs in the anagen phase were immersed in 1% collagenase type IV for 2 hours at 37° C. in order to enzymatically dissociate the hair follicular stem cells from the hair follicle. Hair follicular stem cells were then rinsed several times, and resuspended in culture medium.

Example 3. Collection and Culture of CD34-Positive Cells

CD34-positive cells act as "circulating fibrocytes" and their function is dependent on the environment. For instance, in wound healing CD34-positive cells concentrate around the damaged tissue. In the context of tissue generation, CD34-positive cells act as a stem cell enhancer. Specifically, when hair follicular stem cells are cultured together with CD34-positive cells, hair follicular stem cells are able to proliferate without supplement.

CD34-positive cells were obtained from the peripheral circulation of a donor subject. CD34-positive cells were isolated from the blood using a MACS cell separation kit (Miltenyl Biotec). Isolated CD34-positive cells were then rinsed several time, resuspended in the culture medium (RPMI 1640, GIBCO, Invitrogen) containing autologous serum, and cultured in the same medium for a period of 8 weeks.

Example 4. Preparation of Culture Medium

The culture medium consisted of a sterile Serum Free Growth Medium (Defined Serum Free (Keratinocyte) Growth Medium, purchased from Gibco, USA) which was freshly prepared on the day of the experiment, according to the manufacturer's instructions.

Example 5. Preparation of the Composition for Generating a Desired Cell Type and/or Tissue Type The composition for generating a desired cell type and/or tissue was freshly prepared by adding the following ingredients to the Serum Free Growth Medium described in example 4:
  1 mg/ml of bis(maltolato)oxovanadium (BMOV)
  0.25 mg/ml of mono Hydroxy-Ethyl Rutoside (mono-HER)
  0.25 mg/ml of D-tocopherol acid succinate/α-tocopherol (vitamin E)
  0.1 mg/ml of lipoic acid
  0.1 μmol/ml of adenosine triphosphate-magnesium chloride
  15 mg/ml of deferoxamine mesylate
  $1 \times 10^3$ cells/ml of CD34-positive cells
  0.05 ml/ml of platelet rich plasma
  1 unit/ml of Erythropoietin
  Cell type and/or tissue-type specific differentiation inducing factor: depending on the desired cell type and/or tissue type, a specific additive is added. For instance, to generate neural cell and/or tissue, a basic-fibroblast growth factor is added (see example 6). To generate keratinocyte cell and/or tissue, an epithelial growth factor is added (see example 7). To generate neural cell and/or tissue, a neural growth factor is added (see example 8).

Example 6. Generation of Keratinocyte Cell and/or Tissue

Hair follicular stem cells were enzymatically dissociated from the hair follicular tissue obtained from 10 plucked hairs from a donor subject using collagenase IV (Example 2). Hair follicular stem cells were cultured and expanded for 3 weeks in a three-dimensional culture system in the sterile Serum Free Growth Medium of Example 4. Subsequently, the population of hair follicular stem cells was cultured in the composition of Example 5 comprising epidermal growth factor (100 ng/ml) as the growth factor for a duration of 6 weeks. During this period, the composition comprising the epidermal growth factor was refreshed daily. At the term of the culture period, the keratinocyte cells were harvested and submitted to immunohistological procedures using antibodies directed against keratinocyte markers, i.e. cytokeratins. Cytokeratins 1, 10 and 11 are commonly used markers of differentiating keratinocytes and are exclusively found in the intermediate cells and in the granular cells at the infundibulum in the outer root sheath (ORS) of the human anagen hair follicles. Cytokeratins 19 is a marker of undifferentiated stem cells, and is found in outermost cells of the ORS at the isthmus and in some cells of the lower ORS. Cytokeratins 1, 10, 11, and 19 are used as a reliable keratinocyte markers.

The results show that the newly produced keratinocyte cells and/or tissues were positive for cytokeratins 1, 10, 11, and 19 thus demonstrating that keratinocyte cells and/or tissues can be generated from hair follicular stem cells using the method and composition of the present invention.

Example 7. Generation of Nerve Cell and/or Tissue

Hair follicular stem cells were enzymatically dissociated from the hair follicular tissue obtained from 10 plucked hairs from a donor subject using collagenase IV (Example 2). Hair follicular stem cells were cultured and expanded for 3 weeks in a three-dimensional culture system in the sterile Serum Free Growth Medium of Example 4. Subsequently, the population of hair follicular stem cells was cultured in the composition set forth in Example 5 comprising nerve growth factor (100 ng/ml) as the growth factor for a duration of 6 weeks. During this period, the composition comprising the nerve growth factor was refreshed daily. At the term of the three weeks, nerve cells were harvested. At the term of the culture period, the nerve cells and/or tissues were harvested and submitted to immunohistological procedures using antibodies directed against neural markers, i.e. nestin. Another indication of a neural fate is the absence of the marker keratin 15. Therefore, cells and/or tissues positive for nestin but negative for keratin 15 were reliably identified as neural cells and/or tissues.

The results show that the newly produced nerve cells and/or tissues were positive for nestin and negative for keratin 15, thus demonstrating that nerve cells and/or tissues can be generated from hair follicular stem cells using the method and composition of the present invention.

Example 8: Effect of Vanadium Compounds on Proliferation of Keratinocytes

Method: Hair follicles were transferred to a 24-well culture disk containing dSFK with 500 mg/ml penicillin (Life Technologies B.V. Breda, The Netherlands) and 0.25 µg/ml streptomycin (Life Technologies B.V. Breda, The Netherlands), and placed for 14 days in a culture medium at 31° C. in a humidified atmosphere containing 5% CO2. Three different culture medium were used:

Treatment group oxovanadium (OVAN): The culture medium is a composition comprising a basic SFK growth serum (purchased from the supplier SFK, Enschede The Netherlands) supplemented with either 1 mg/ml of OVAN.

Treatment group bis (maltolato) oxovanadium (BMOV): The culture medium is a composition comprising a basic SFK growth serum (purchased from the supplier SFK, Enschede The Netherlands) supplemented with either 1 mg/ml of BMOV.

Control group: The control situation consists of a composition comprising the SFK basic growth serum but without the vanadium compounds (i.e. OVAN or BMOV).

The respective culture media were carefully removed every three days and replaced by fresh culture media. The cells remained attached to the hair follicles during this culture period. After 14 days the culture medium was removed and replaced by a 0.5 mg/ml trypsin, 0.2 mg/ml EDTA (ethylene diaminetetraacetic acid) solution (Life Technologies B.V. Breda, The Netherlands), and incubated for 5 minutes at 37° C. in this medium. After this incubation period clusters of cells were released from the hair follicles. These were harvested by centrifugation at 300 g at 4° C. for 5 minutes in an Eppendorf 5804R Centrifuge (VWR International, The Netherlands). Number of cells were counted and expressed as amount of proliferated cells per ml of culture medium.

Results:

The results show that the amount of proliferated keratinocytes was significantly increased following treatment with both vanadium compounds, i.e. OVAN and BMOV relative to the control situation. The results further show that BMOV appears to be more potent than OVAN. Overall, these results show that vanadium compounds are particularly effective at promoting cell proliferation as well as cell survival under culture condition (see FIG. 1).

What is claimed is:

1. A method for differentiating at least one hair follicular stem cell specifically into keratinocytes, said method involving contacting at least one hair follicular stem cell with a composition wherein the one physiologically acceptable vanadium compound enhances proliferation of keratinocytes comprising at least one physiologically acceptable vanadium compound, at least one antioxidant compound, at least one stem cell enhancer compound, at least one extracellular matrix compound, and at least one differentiation inducing factor, wherein the one physiologically acceptable vanadium compound is bis(maltolato)oxovanadium in a concentration of 0.01-100 mg/ml, and the stem cell enhancer compound is erythropoietin, and the one differentiation inducing factor is epithelial growth factor, to thereby obtain keratinocytes.

2. The method according to claim 1, wherein the composition further comprises one or more anti-apoptotic compounds selected from the group consisting of triiodothyronine, estradiol, progesterone, bovine pituitary extract, insulin and adenosine triphosphate-magnesium chloride.

3. The method according to claim 1, wherein the antioxidant compound is selected from the group consisting of quercetin, monohydroxyethyl rutoside, vitamin C, lipoic acid, deferoxamine mesylate, and vitamin E.

4. The method of according to claim 1, wherein the stem cell enhancer compound further comprises retinoic acid.

5. The method of according to claim 1, wherein the stem cell enhancer compound further comprises CD34-positive cell.

6. The method according to claim 1, wherein the composition further comprises at least one degranulating agent selected from the group consisting of Compound 48/80 and Compound 48/80 with $CaCl_2$.

7. The method according to claim 6, wherein the degranulating agent is Compound 48/80.

8. The method of according to claim 1, wherein the extracellular matrix compound is selected from the group consisting of: laminin, collagen IV, heparan sulfate, entactin, and chondroitin sulfate.

9. The method according to claim 1, wherein the composition further comprises platelet rich plasma.

10. The method according to claim 1, wherein the at least one hair follicular stem cell is obtained from at least a part of a hair follicle in the anagen phase.

11. The method according to claim 10, wherein the at least a part of a hair follicle in the anagen phase has been obtained by plucking a hair from a donor area of a subject.

12. The method according to claim 10 wherein the at least a part of a hair follicle is contacted with a medium comprising collagenase IV.

13. The method according to claim 1, wherein the at least one hair follicular stem cell is a human hair follicular stem cell.

14. The method according to claim 1, wherein the keratinocytes are introduced in a recipient region in a subject, and wherein the at least one hair follicular stem cell is derived from said subject, and wherein the composition comprises at least one CD34-positive cell derived from said subject and/or platelet rich plasma derived from said subject.

15. The method according to claim 1, wherein the is keratinocytes are used for regenerative medicine.

16. The method according to claim 1, wherein the keratinocytes are used for cosmetic purpose.

* * * * *

UNITED STATES PATENT AND TRADEMARK OFFICE
CERTIFICATE OF CORRECTION

| | |
|---|---|
| PATENT NO. | : 11,840,706 B2 |
| APPLICATION NO. | : 16/282444 |
| DATED | : December 12, 2023 |
| INVENTOR(S) | : Conradus Ghosal Gho |

It is certified that error appears in the above-identified patent and that said Letters Patent is hereby corrected as shown below:

On the Title Page

Item (22), delete "Jul. 13, 2023" and insert -- Feb. 22, 2019 --.

Signed and Sealed this
Second Day of April, 2024

Katherine Kelly Vidal
*Director of the United States Patent and Trademark Office*